United States Patent [19]
Cimber

[11] Patent Number: 5,555,896
[45] Date of Patent: Sep. 17, 1996

[54] INTRAUTERINE CONTRACEPTIVE DEVICE

[76] Inventor: Hugo Cimber, Bernstrasse 34, Ch-3072 Ostermundigen, Switzerland

[21] Appl. No.: 532,295

[22] Filed: Sep. 22, 1995

[30] Foreign Application Priority Data

Sep. 26, 1994 [EP] European Pat. Off. .............. 94810559

[51] Int. Cl.⁶ .................................................. A61F 6/06
[52] U.S. Cl. ........................................ 128/830; 128/831
[58] Field of Search ..................... 128/830–841

[56] References Cited

U.S. PATENT DOCUMENTS

| | | | |
|---|---|---|---|
| 3,042,030 | 7/1962 | Read | 128/831 |
| 3,805,767 | 4/1974 | Erb | 128/831 |
| 3,880,156 | 4/1975 | Hoff . | |
| 4,353,363 | 10/1982 | Quesada | 128/833 |
| 4,365,621 | 12/1982 | Brundin | 128/831 |
| 4,578,076 | 3/1986 | Luukkainen | 128/833 |

FOREIGN PATENT DOCUMENTS

| | | |
|---|---|---|
| 0208653 | 1/1987 | European Pat. Off. . |
| 2085578 | 12/1971 | France . |
| WO91/00714 | 1/1991 | WIPO . |

*Primary Examiner*—Michael A. Brown
*Attorney, Agent, or Firm*—Townsend and Townsend and Crew

[57] ABSTRACT

The intrauterine contraceptive device to be inserted in the uterus comprises a supporting stem (1) having two branches (4) disposed at the front end (3) thereof in the direction of insertion. Each of the branches bears at its free end a permanent closure member (7). The closure members are intended to seal the mouths of the Fallopian tubes into the uterus. Each closure member is made of a soft material and has a substantially spherical or tear-shaped form. Fixed to these closure members is a temporary holding and positioning rod (9) of flexible, resorbable material, e.g., of collagen or polyglycolic acid, in such a way that this holding and positioning rod, together with the supporting stem (1), forms the shape of a T, the positioning ends (10) of the holding and positioning rod (9) being farther apart than the permanent closure members (7). The intrauterine contraceptive device is suitable for use immediately after a pregnancy. Insertion in the uterus is easily possible at that time through the still open uterine orifice without the diameter of the insertion means having to be kept minimal. Moreover, the temporary holding and positioning rod takes over the function of a sealing means for the mouths of the Fallopian tubes. It also retains this function during its biodegradation, during the interval when the uterus, still stretched after the pregnancy, undergoes involution within a period of six weeks. Thereafter, the permanent closure members (7) take over the sealing function.

9 Claims, 1 Drawing Sheet

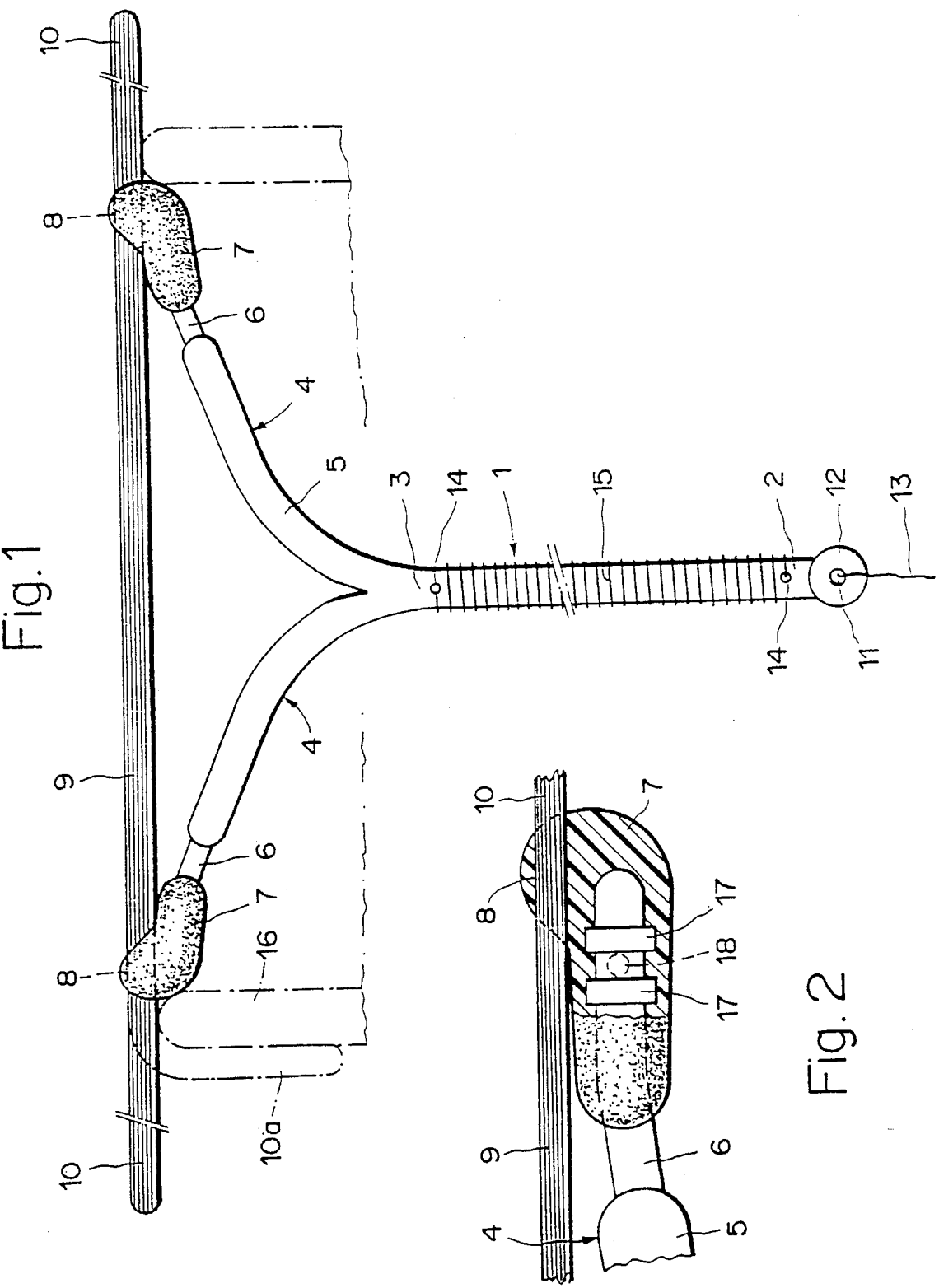

INTRAUTERINE CONTRACEPTIVE DEVICE

The present invention relates to an intrauterine contraceptive device, suitable for being used immediately after a pregnancy.

Intrauterine contraceptive devices are known in which two branches capable of spreading apart are expelled from a small tube, the branches bearing closure means at their ends. Thus, for example, an intrauterine contraceptive device is known from FR-A-2,085,578 which is inserted into the uterus by means of a small tube, a supporting stem being provided with two branches hinged to its front end in the direction of insertion, in such a way that the branches spread laterally apart after their expulsion from the tube. At their free ends, the branches each bear a spherical closure member, which closure members are intended and suitable for closing off the mouths of the Fallopian tubes into the uterus. The branches are of approximately equal length so that the two closure members come to lie next to one another upon retraction of the intrauterine device into the tube, and the tube must thus have a comparatively large diameter. According to EP-A-0,208,653, the aim in intrauterine contraceptive devices is to keep the diameter of the tube as small as possible since, as is well known, the smaller the tube diameter is, the easier and more agreeable is the insertion of such tubes. This diameter, in turn, is substantially dependent upon the mutual position in which the closure members at the ends of the mentioned branches can be pulled into the tube. Contrary to the first-mentioned French document, it is provided in the second-mentioned text that one of the branches is provided with at least one predetermined buckling location so that with the branches pulled into the tube, the spherical closure members come to lie one behind the other as viewed in the direction of retraction and not next to one another. Until now, in the case of women who had just undergone parturition, it has been necessary to delay the insertion of an intrauterine contraceptive device for about six weeks so that the uterus could revert to its original size because otherwise the intrauterine device would in all probability be ejected again. Thus there is a need for an intrauterine device, the insertion of which can be carried out immediately after parturition. This has not been possible with the previously known intrauterine devices since the distance between the closure members of the prior art intrauterine devices corresponds to the distance between the mouths of the Fallopian tubes in the post-involutional state. Immediately after parturition, the uterus is about 12 cm wide and 17 cm long; the uterine orifice then has a diameter of from 3 to 4 cm. In the post-involutional state, about six weeks after parturition, the uterus is about 4 cm wide and 7 cm long, and the uterine orifice is from 3–4 mm. Thus, immediately after parturition the prerequisites for insertion of an intrauterine device would be very favourable owing to the open cervical os since insertion can take place during a concluding examination of the woman prior to her release from the hospital. For this purpose, the intrauterine device must be designed in such a way that it can also perform its task during the six weeks of involution of the uterus, i.e., it must remain in the correct position after insertion, and at the same time the closure members must carry out their sealing function. Until now, no such intrauterine devices have been available.

It is thus the object of the present invention to provide an intrauterine contraceptive device which is so designed that in comparison with the prior art, it can be inserted immediately after a pregnancy, a positioning and holding means being adapted to the lessening dimensions simultaneously with the involution of the uterus.

According to the invention, this problem is solved by means of an intrauterine contraceptive device having the features of the characterizing clause of the present invention.

Preferred embodiments are characterized by the features of the drawings in the present invention.

The holding and positioning rod of resorbable or biodegradable material which, by means of its positioning ends, also makes temporary closure members available for the mouths of the Fallopian tubes during involution of the uterus, if need be, has a length of about 12 cm (corresponding to the postpartum width of the uterus) and is fixed to the permanent closure members in such a way that the latter can take over their function after the breakdown of the holding and positioning rod. Its two positioning ends are preferably rounded or made of soft material. The resorbable or biodegradable material is, for instance, suture material such is used for making surgical stitches and comprises, e.g., collagens such as catgut; polyglycolic acid or polyglyconate. One such product is, for instance, Maxon (polyglyconate) from the firm Davies & Geck, Gosport, Hampshire, U.K. The material is said to have a degree of cross-linking such that the holding and positioning rod is resilient enough to permit insertion without any problems and is nonetheless stable enough thereafter to be able to exercise the temporary closure and holding function. Furthermore, the thickness and structure of the resorbable suture material is so chosen that breakdown takes place within six weeks. At least partial sheathing of the holding and positioning rod was additionally able to serve that purpose. The material for the sheathing might be products having defined biodegradability such as are utilized in delayed-release medication.

The permanent closure members should as a rule have a substantially rounded shape in order to seal the mouths of the Fallopian tubes into the uterus. It is consequently preferably if the permanent closure members, which take over their function after involution of the uterus, meet these prerequisites.

Since the intrauterine device is intended for use directly after parturition, the tube for its insertion need not be particularly thin, as is the case with normal intrauterine devices, but may have a thickness of up to 3.6 cm. With this diameter, the tube can be inserted without difficulty in the cervical os still open after parturition. This has the advantage that the intrauterine device need undergo little or no deformation and is nevertheless optimally protected prior to its positioning.

When the intrauterine device is pulled into the small tube, the two branches spreading away from the supporting stem have hitherto been pressed together, and the approximately plane faces of the two closure members fixed one on each free end of the branches came to rest against one another or one over the other. Since, however, the temporary holding and positioning rod of the intrauterine device according to the present invention is affixed to the permanent closure members, deformation is somewhat problematic. Yet because the insertion tube may be up to 3.6 cm thick, the intrauterine device without holding and positioning beam can be pushed into the tube practically undeformed. Only the terminal portions of the holding and positioning rod disposed at right angles to the longitudinal axis of the tube project laterally beyond the latter. Because of its resilient deformability, the two projecting positioning ends of the holding and positioning rod can now be bent down in such a way that they rest against the outside of the tube. When the intrauterine device is substantially in position in the uterus, the holding and positioning rod may again assume its original shape, and its positioning ends can act as temporary closure members of the mouths of the Fallopian tubes. The holding and positioning rod simultaneously holds the intrauterine device in correct position during involution of the uterus. After about six weeks, the uterus has reverted to its original size, and the holding and positioning rod has disintegrated. The permanent closure members are now automatically positioned at the mouths of the Fallopian tubes, and the intrauterine device corresponds in shape and function to an ordinary intrauterine contraceptive device.

It has proven advantageous if the tube with the intrauterine device is inserted in the open uterine orifice immediately after parturition, thus avoiding any risk of injuring the uterus upon insertion of the intrauterine device. The rounded holding and positioning rod of resorbable resilient material has an additional protective function in this connection.

When the sealing rod has disintegrated, the permanent closure members are disposed on the branches in such a way that they are on the side remote from the supporting stem. The closure members are formed so that their substantially rounded free ends rest gently and softly against the uterine mucous membrane in the area of the mouths of the Fallopian tubes and thereby seal these mouths tight. Owing to the softness of the material of the closure members, there is an adaptation to the particular circumstances of the uterus. The two closure members are extremely mobile and soft and are preferably made with a silicone-base material. The supporting stem and the two branches are preferably made in one piece and may be of any stiff material. A suitable plastic has proved to be polyethylene, for example.

During manufacture of the intrauterine device, the two branches have been carried out in such a way that they extend arcuately away from the supporting stem. Owing to the rigidity and resiliency of the material, the two branches can be joined, if necessary, when the intrauterine device is pulled into the tube; and thanks to their resiliency, they again assume the shape predetermined during manufacture when the intrauterine device is expelled from the tube. Removal of the intrauterine device without difficulty is also made possible thereby.

In a further embodiment of the intrauterine device, each branch may have a bend about halfway between the supporting stem and the closure member.

The mentioned branches with the permanent closure members are connected by the holding and positioning rod. This connection is usually free of tension. In a particular embodiment of the invention, the holding and positioning rod may be fixed in such a way that the two branches are mutually under tension. It may thereby be achieved that the branches with the permanent closure members cannot assume the desired final position with a greater or lesser mutual spacing until after complete disintegration of the holding and positioning rod.

Preferred embodiments of the present invention are described in detail by way of example with the aid of drawing figures.

FIG. 1 shows the subject of the invention with a small tube, with a holding and positioning rod placed upon the branches, in a diagrammatic view, and FIG. 2 shows the arrangement of a permanent closure member at a free end of a branch.

In the depicted exemplary embodiment according to FIG. 1, the intrauterine device has a supporting stem 1, the rearward end 12 of which in the direction of insertion (distal end) is provided with an eye 11 for looping through an extraction thread 13, whereas at the other (proximal) end 3, the forward end in the direction of insertion, two branches 4 are disposed, made of the same material as the supporting stem and extending arcuately away from the supporting stem 1. The branches 4 are resiliently disposed in such a way that insertion and, above all, removal is possible without difficulty and without risk of injury. The rearward end 12 is spherical or tear-shaped and can thus not penetrate into the mucous membrane of the uterus. The supporting stem 1 is preferably wound with copper wire 13, the contraceptive action of which is quite generally known. At both ends 2, 3 of the supporting stem 1, bores 14 are provided in which the ends of the wire may be fastened.

Each branch 4 comprises, extending arcuately away from the supporting stem 1, a positioning portion 5, adjoining the end of which nearest the supporting stem 1 is an extension 6. The extension 6 is intended to have a permanent closure member 7 disposed at its free end. The extension 6 is made with a smaller diameter than the positioning portion 5, whereby it is achieved that the permanent closure member is movable relative to the positioning portion 5 and, after disintegration of a temporary holding and positioning rod 9, can seek out the most favourable position for sealing the mouths of the Fallopian tubes. Each closure member 7, having substantially the shape of a spherical or tear-shaped body, has an integral holding means 8 for the holding and positioning rod 9 of resorbable suture material, the holding and positioning rod being disposed at right angles to the supporting stem 1; the supporting stem 1 and the holding and positioning rod 9 thus form the shape of a T. Further apparent from FIG. 1 is the position of the intrauterine device in a small tube 16 serving as an aid to insertion. Moreover, the positioning ends 10 of the holding and positioning rod 9 project out of the tube 16. During the insertion operation, the positioning ends 10 of the flexible and resilient holding and positioning rod are bent in such a way that they assume a position 10a parallel to the supporting stem 1. The tube 16 is so formed that the intrauterine device is centrally disposed and can easily be ejected. For avoiding a risk of injury, the edges of the tube are rounded at the proximal end.

Starting from a position as indicated, the intrauterine contraceptive device is inserted in the uterus by means of the tube 16, a rod (not shown) serving to push the intrauterine device within the tube 16 forward, i.e., out of the tube. As already stated, the part of the temporary holding and positioning rod projecting from the tube additionally protects the uterus from possible injuries.

As soon as the intrauterine device within the insertion tube 16 is pushed forward far enough, the holding and positioning rod, owing to the resiliency of its material, again assumes its original straight shape in which the positioning ends 10, to start with spaced about 12 cm apart, rest against the uterine mucous membrane gently and softly in the area of the mouths of the Fallopian tubes and thereby already seal these mouths tight immediately after a pregnancy. At this moment, the biodegradation of the resorbable material of the holding and positioning rod begins in the uterine environment, the closure function being maintained, however.

Owing to the softness of the material of the closure members 7, as well as the mobility of the extensions 6, adaptation of the closure members 7 to the particular circumstances of the uterus is made possible after disintegration of the holding and positioning rod 9.

The intrauterine device is customarily taken out by means of the thread 13 looped through the eye 11 in that when this thread is pulled, the supporting stem 1 and the branches 4 of the intrauterine device collapsible through resilient deformation can be pulled out through the cervix.

In FIG. 2, it is shown how the closure member 7 is attached to the extension 6. The free end of the extension 6 remote from the positioning portion 5 of the branch 4 projects into the closure member 7. In this region there are ribs 17 and/or a bore 18 on the extension 6 in order to ensure faultless holding of the permanent closure member 7. The latter is preferably injection moulded on the end of the extension 6. Instead of the mentioned ribs, grooves might naturally also be provided, which are not depicted in the drawing of the exemplary embodiment shown. The permanent closure members have on their proximal side, substantially parallel to the extension 6, a through bore intended to receive the temporary holding and positioning rod in such a way that the latter and the supporting stem 1 together form a T. Once the temporary holding and positioning rod is removed by biodegradation, the permanent closure member takes over its function, the through bore being of no inconvenience whatever since the rounded surfaces on the other side of the closure member 7 take over the closing function.

The intrauterine contraceptive devices described make it possible to ensure reliable closure of the mouths of the Fallopian tubes in the most gentle way, avoiding any irritation of the uterus and ensuring free discharge of the menstrual blood, and they can be inserted just as painlessly as removed. Manufacture presents no particular problems, so that the intrauterine devices shown are capable of being supplied for wide dissemination.

I claim:

1. Intrauterine contraceptive device which can be inserted in the uterus by means of a small tube (16), containing a supporting stem (1) and, disposed at the front end (3) thereof in the direction of insertion, two branches (4) laterally spread apart, the branches (4) each bearing at their free ends a permanent closure member (7), which closure members (7) are intended and suitable for sealing the mouths of the Fallopian tubes into the uterus, each of the branches (4) comprising a comparatively stiff positioning portion (5) as well as a thin, flexible, and movable extension (6) disposed at the free end of the positioning portion (5), on which extension (6) the permanent closure member (7) is disposed, each closure member (7) being formed of a soft material, characterized in that a temporary holding and positioning rod (9) with positioning ends (10) is disposed on the two closure members (7) in such a way that together with the supporting stem (t) it substantially forms the shape of a T, the holding and positioning rod being made of resorbable material.

2. Intrauterine contraceptive device according to claim 1, characterized in that the resorbable material is resorbable suture material of collagen, polyglycolic acid, or polyglyconate.

3. Intrauterine contraceptive device according to claim 1, characterized in that the two permanent closure members (7) have on their proximal side, aligned substantially parallel to the extension (6), through bores (8) serving to receive the temporary holding and positioning rod (9).

4. Intrauterine contraceptive device according to claim 1, characterized in that the two branches (4) extend arcuately away from the supporting stem (1).

5. Intrauterine contraceptive device according to claim 1, characterized in that about halfway between the supporting stem (1) and the closure member (7), each of the branches (4) has a bent location.

6. Intrauterine contraceptive device according to claim 1, characterized in that the temporary holding and positioning rod has a length of about 12 cm.

7. Intrauterine contraceptive device according to claim 1, characterized in that the spacing of the permanent closure members is from 3–3.5 cm.

8. Intrauterine contraceptive device according to claim 1, characterized in that the diameter of the small tube (16) is about 3.6 cm.

9. Intrauterine contraceptive device according to claim 1, characterized in that the positioning ends (10) are rounded and/or are made of soft material.

* * * * *